(12) United States Patent
Hennings et al.

(10) Patent No.: US 11,432,745 B2
(45) Date of Patent: Sep. 6, 2022

(54) GAIT DETECTION ALGORITHM (71) Applicant: NORDIC-NEUROSTIM APS, Aalborg Öst (DK)

(72) Inventors: Kristian Hennings, Aalborg SV (DK); Morten Hansen, Storvorde (DK)

(73) Assignee: NORDIC-NEUROSTIM APS

( * ) Notice: Subject to any disclaimer, the term of this patent is extended or adjusted under 35 U.S.C. 154(b) by 251 days.

(21) Appl. No.: 16/067,451

(22) PCT Filed: Jan. 4, 2017

(86) PCT No.: PCT/EP2017/050148
§ 371 (c)(1),
(2) Date: Jun. 29, 2018

(87) PCT Pub. No.: WO2017/118664
PCT Pub. Date: Jul. 13, 2017

(65) Prior Publication Data
US 2020/0268282 A1 Aug. 27, 2020

(30) Foreign Application Priority Data
Jan. 8, 2016 (SE) .................................. 1650021-7

(51) Int. Cl.
*A61B 5/103* (2006.01)
*G16H 20/30* (2018.01)
(Continued)

(52) U.S. Cl.
CPC .......... *A61B 5/1038* (2013.01); *A61B 5/6807* (2013.01); *A61B 5/7246* (2013.01);
(Continued)

(58) Field of Classification Search
CPC ... A61B 5/1038; A61B 5/6807; A61B 5/7246; A61B 2505/09; G16H 40/67; G16H 20/30; G01L 15/00; G01L 19/00; G01L 19/0092
See application file for complete search history.

(56) References Cited

U.S. PATENT DOCUMENTS 5,033,291 A 7/1991 Podoloff et al.
5,323,650 A 6/1994 Fullen et al.
(Continued)

FOREIGN PATENT DOCUMENTS

JP 2012-085891 A 5/2012
JP 2014-045885 A 3/2014
(Continued)

*Primary Examiner* — Randy W Gibson
*Assistant Examiner* — John M Royston
(74) *Attorney, Agent, or Firm* — Condo Roccia Koptiw LLP (57) ABSTRACT

A method in gait rehabilitation for detecting a foot being lifted comprises: receiving (102) a plurality of signals from respective pressure sensors (12), mounted beneath a foot of a person, each signal providing a time sequence of values representing asserted pressure; processing the received signals, wherein said processing comprises, for each signal, assigning states to the respective pressure sensor (12) for determining when the foot is being lifted for walking, and wherein said assigning of states comprises: identifying that the sequence of values are maintained above an upper threshold (32) for a duration exceeding a time threshold (36); and upon such identifying assigning a prepared state to the sensor (12); and, when the sensor (12) is in the prepared state, identifying (108) a value below a lower threshold (34) indicating that the foot is potentially lifted; and upon such identifying assigning an unprepared state to the sensor (12); and wherein said processing further comprises, when assigning an unprepared state to a first sensor, determining (110)

(Continued)

whether a prepared state is assigned to a second sensor and comparing (112) a priority of the first sensor and the second sensor.

20 Claims, 3 Drawing Sheets

(51) Int. Cl.
    *G16H 40/67*            (2018.01)
    *A61B 5/00*             (2006.01)
    *G01L 19/00*            (2006.01)
    *G01L 15/00*            (2006.01)

(52) U.S. Cl.
    CPC ............. *G16H 20/30* (2018.01); *G16H 40/67* (2018.01); *A61B 2505/09* (2013.01); *G01L 15/00* (2013.01); *G01L 19/00* (2013.01); *G01L 19/0092* (2013.01)

(56) References Cited

U.S. PATENT DOCUMENTS

| | | |
|---|---|---|
| 5,814,093 A | 9/1998 | Stein |
| 8,788,049 B2 | 7/2014 | Lasko et al. |
| 2010/0057398 A1 | 3/2010 | Darley et al. |
| 2011/0009241 A1 | 1/2011 | Lane et al. |
| 2011/0054358 A1 | 3/2011 | Kim et al. |
| 2013/0006152 A1 | 1/2013 | Lee et al. |
| 2013/0096466 A1 | 4/2013 | Sarrafzadeh et al. |
| 2013/0236867 A1 | 9/2013 | Avni et al. |
| 2014/0039657 A1 | 2/2014 | Spector |
| 2014/0195023 A1 | 7/2014 | Statham et al. |
| 2015/0080979 A1 | 3/2015 | Lasko et al. |
| 2016/0324445 A1* | 11/2016 | Kim .................... A61B 5/1038 |
| 2017/0281085 A1* | 10/2017 | Lee ......................... G06F 19/34 |

FOREIGN PATENT DOCUMENTS

| | | |
|---|---|---|
| JP | 2015-202141 A | 11/2015 |
| KR | 10-2014-0066341 A | 6/2014 |

* cited by examiner

GAIT DETECTION ALGORITHM

CROSS REFERENCE TO RELATED APPLICATIONS

This application is the National Stage Entry under 35 U.S.C. § 371 of Patent Cooperation Treaty Application No. PCT/EP2017/050148, filed 4 Jan. 2017, which claims priority from Swedish Application No. 1650021-7, filed 8 Jan. 2016, the contents of which are hereby incorporated by reference herein.

TECHNICAL FIELD

The present invention relates to a method and a device for use in gait rehabilitation for detecting a foot being lifted.

BACKGROUND

A patient suffering from deteriorated ability to walk is severely affected by such a condition. The inability to walk may for instance be caused by a disease or trauma to the central nervous system, such as stroke, spinal cord injury, and multiple sclerosis.

For such patients, gait rehabilitation is an important step to improve quality of life of the patient. Gait rehabilitation may involve providing the patient with an electrical stimulation, which may induce a withdrawal reflex activating nerves of the patient to cause a muscle contraction such that a foot is lifted. Electrical stimulation may thus be used in training for restore ability of the patient to send nerve signals for lifting the foot.

There are known methods of providing electrical stimulation for providing a patient with an improved gait. For instance, in U.S. Pat. No. 8,788,049 a gait modulation system is disclosed comprising a sensor for transducing at least one parameter related to gait of the patient and a muscle stimulator for performing functional electrical stimulation of at least one muscle of the lower limb. The system may be used constantly, such that the system helps the patient to properly walk. However, this also implies that the system needs to be able to determine when a patient is not walking, such that unintended stimulations are not provided.

SUMMARY OF THE INVENTION

It is an object of the invention to provide simple and reliable detection of a foot being lifted. The detection may thus e.g. be used for timing of electrical stimulation or for analysis of the gait of a patient.

These and other objects of the invention are at least partly met by the invention as defined in the independent claims. Preferred embodiments are set out in the dependent claims.

According to a first aspect of the invention, there is provided a method in gait rehabilitation for detecting a foot being lifted, said method comprising: continuously receiving a plurality of signals from respective pressure sensors, which are mounted beneath a foot of a person in order to record a pressure asserted by the person against ground when walking, each signal providing a time sequence of values representing asserted pressure on the respective pressure sensor; processing the received plurality of signals, wherein said processing comprises, for each signal, assigning states to the respective pressure sensor for determining when the foot is being lifted for walking, and wherein said assigning of states comprises: comparing the values representing asserted pressure to an upper threshold and identifying a value above the upper threshold, upon identifying a value being above the upper threshold, comparing the sequence of values to the upper threshold and determining a duration during which the sequence of values are continuously above the upper threshold; comparing the determined duration to a time threshold and identifying that the sequence of values are maintained above the upper threshold for a duration exceeding the time threshold; and upon identifying a duration exceeding the time threshold assigning a prepared state to the sensor; and when the sensor is in the prepared state, comparing the sequence of values to a lower threshold and identifying a value below the lower threshold providing an indication that the foot is potentially lifted; and upon identifying a value below the lower threshold assigning an unprepared state to the sensor.

Thanks to the invention, the lifting of a foot may be detected by relatively simple processing of recorded signals. The detection of lifting of a foot is not related to a periodicity of steps, such that each time a foot is lifted, it is individually detected.

Such detection may be especially advantageous in gait rehabilitation, wherein a training phase for teaching the patient to walk is utilized. The training phase may make use of powerful electrical stimulations for causing the withdrawal reflex. Thus, the method in gait rehabilitation may not be used continuously, but rather during limited periods of training. Then, it may not be relevant to determine whether the foot is lifted for changing weight or whether the foot is lifted for walking.

By detecting that asserted pressure has been applied during a period of time and, then, detecting that asserted pressure decreases below a lower threshold, an indication that the foot is lifted is identified. Thus, a simple way of detecting that a foot is lifted is provided. The asserted pressure needs to be applied during a substantial period of time, in order for the sensor to be assigned a prepared state. Hence, a detection of the foot being lifted is not done when a pressure is briefly asserted, such as may occur when the patient is sitting.

According to an embodiment, said processing further comprises, when assigning an unprepared state to a first sensor, determining whether a prepared state is assigned to a second sensor and comparing a priority of the first sensor and the second sensor.

The invention according to this embodiment may enable the detection of a foot being lifted to be related to a position of the foot where pressure is asserted. This implies that a reliable detection of a foot being lifted may be performed even for patients that have trouble to lift the entire foot.

The priorities of the first and second sensors may thus be advantageously used for determining lifting of a foot for persons having impaired gait so as to enable use of the detection of a foot being lifted as input for stimulating gait. For instance, the priorities of the pressure sensors may be used for successfully detecting lifting of a foot for persons having a gait where the heel never touches the ground and for persons having a gait where the heel touches the ground, but the forefoot never leaves the ground.

According to a second aspect of the invention, there is provided a device for use in gait rehabilitation for detecting a foot being lifted, said device comprising: at least one input contact for continuously receiving a plurality of signals from respective pressure sensors, which are mounted beneath a foot of a person in order to record a pressure asserted by the person against ground when walking, each signal providing a time sequence of values representing asserted pressure on the respective pressure sensor; a processing unit, wherein said processing unit is configured to process the received plurality of signals, wherein said processing comprises, for each signal, assigning states to the respective pressure sensor for determining when the foot is being lifted for walking, and wherein said assigning of states comprises: comparing the values representing asserted pressure to an upper threshold and identifying a value above the upper threshold, upon identifying a value being above the upper threshold, comparing the sequence of values to the upper threshold and determining a duration during which the sequence of values are continuously above the upper threshold; comparing the determined duration to a time threshold and identifying that the sequence of values are maintained above the upper threshold for a duration exceeding the time threshold; and upon identifying a duration exceeding the time threshold assigning a prepared state to the sensor; and when the sensor is in the prepared state, comparing the sequence of values to a lower threshold and identifying a value below the lower threshold providing an indication that the foot is potentially lifted; and upon identifying a value below the lower threshold assigning an unprepared state to the sensor.

According to an embodiment, said processing further comprises, when assigning an unprepared state to a first sensor, determining whether a prepared state is assigned to a second sensor and comparing a priority of the first sensor and the second sensor.

The device according to the second aspect of the invention may be used for implementing the method according to the first aspect of the invention.

According to an embodiment of the method, said processing further comprises, when assigning an unprepared state to a first sensor, providing a trigger signal for stimulating gait of the person on a condition that no other sensor with a higher priority is in a prepared state.

Hence, the method may be used for timing of trigger signals for providing an electrical stimulation in gait rehabilitation. By means of the trigger signal only being provided on condition that no other sensor with a higher priority is in a prepared state, the method may ensure that the trigger signal is not falsely provided, when only an insignificant part of the foot is lifted.

However, it should be understood that the method may be used also for mere analysis of the gait, which may be used e.g. in designing a gait rehabilitation for the patient. Thus, the method may include merely detecting when a foot is lifted, which detection may then be used as data for performing an analysis of the gait.

According to an embodiment, said assigning of states further comprises assigning the unprepared state to all sensors, when a trigger signal is provided. This implies that when a first sensor having a high priority detects a foot being lifted to cause the trigger signal to be provided, a second sensor that may also be in a prepared state may not shortly thereafter cause another trigger signal to be provided by means of the pressure value of the second sensor also falling below the lower threshold.

According to an embodiment, said assigning of states further comprises, when the sensor is in the unprepared state and a value of the signal is below the lower threshold, maintaining the sensor in the unprepared state until a predetermined time period has lapsed and thereafter assigning a ready state to the sensor, wherein, after an unprepared state has been assigned to the sensor, said assigning of the prepared state to the sensor is only possible if the ready state has first been assigned to the sensor.

This implies that after a trigger signal has been provided, a predetermined time period must lapse, before a sensor may be brought into the prepared state. Thus, two subsequent trigger signals may not be provided within an interval less than the predetermined time period.

According to an embodiment, the predetermined time period is at least 150 ms. The predetermined time period may be set to ensure that subsequent trigger signals may not be provided within an unrealistically small interval. For patients having relatively normal gait, the predetermined time period may be set to at least 150 ms.

However, the predetermined time period may be set to other values. For instance, if the method is to be used on a patient having severely impaired gait, the predetermined time period may be set to at least 400 ms, or even, 500 ms.

According to an embodiment, a priority of each of the sensors is pre-set in a processing unit for processing the received plurality of signals. Thus, the sensors may be set up to have appropriate priorities before gait rehabilitation is started. Such priorities may be provided on manufacture or installation of a system for use in gait rehabilitation.

According to another embodiment, the method further comprises, before receiving signals from the pressure sensors, receiving an indication of the priority of each of the sensors. Thus, the priority of the sensors may be set, e.g. when a patient is prepared for gait rehabilitation. This may for instance imply that a sensor may be freely positioned on a foot of the patient, and the priority of the sensor may be set depending on in what position on the foot the sensor was positioned.

According to an embodiment, the plurality of sensors include a heel sensor, adapted and intended for mounting on a heel of the person, a lateral forefoot sensor, adapted and intended for mounting on a lateral forefoot of the person, and a medial forefoot sensor, adapted and intended for mounting on a medial forefoot of the person.

According to an embodiment, the heel sensor is set to have the highest priority. The heel sensor may thus detect lifting of a foot even if the forefoot never leaves the ground in an impaired gait of a person.

According to an embodiment, the time threshold is at least 70 ms. This implies that a pressure needs to be asserted at least during 70 ms in order to allow a sensor to be assigned a prepared state.

BRIEF DESCRIPTION OF DRAWINGS

The above, as well as additional objects, features and advantages of the present inventive concept, will be better understood through the following illustrative and non-limiting detailed description of preferred embodiments of the present invention, with reference to the appended drawings. In the drawings like reference numerals will be used for like elements unless stated otherwise.

DETAILED DESCRIPTION

Detailed embodiments of the present invention will now be described with reference to the drawings.

Figure 1:
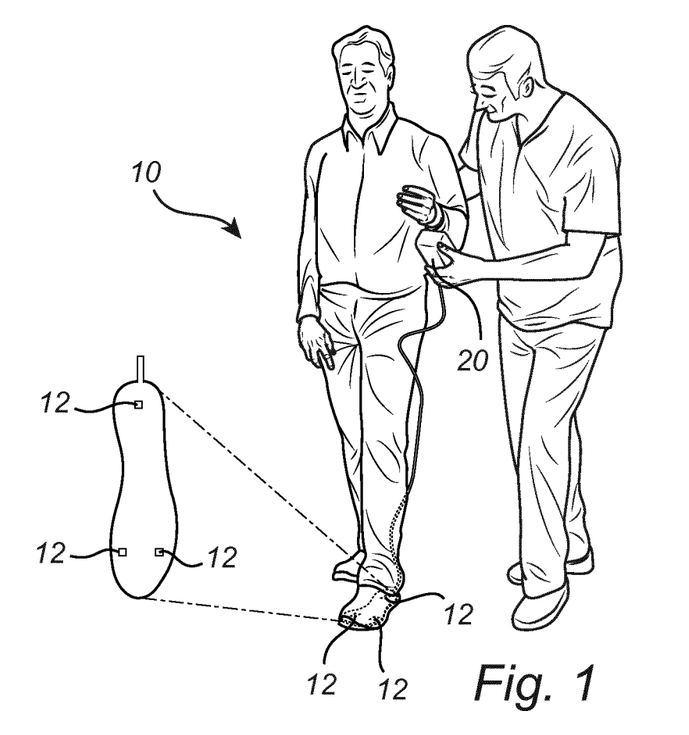
FIG. 1 is a schematic view of a system for use in gait rehabilitation.

Referring now to FIG. 1, a system 10 for use in gait rehabilitation will be first explained. The system 10 may be used by a caregiver, which may monitor and provide a treatment to a patient having an impaired gait.

The system 10 may comprise a plurality of pressure sensors 12. The pressure sensors 12 may be adapted to be mounted beneath a foot of the patient. The pressure sensors 12 may for instance be arranged to be attached to a foot sole of the patient, e.g. by having a sticky surface which may be applied to the foot sole.

According to an embodiment, a plurality of pressure sensor 12 may be arranged on a common carrier. The carrier may have a shape corresponding to a foot and may thus fit to be arranged as an insole in a shoe of the patient.

The pressure sensors 12 may be arranged to record a pressure asserted by the patient, when the pressure sensors 12 are mounted beneath the foot. Each pressure sensor 12 may thus be arranged to generate a sequence of pressure measurements.

Each pressure sensors 12 may further comprise a communication unit, such that the pressure sensor 12 may communicate the generated sequence of pressure measurements to an external unit.

The pressure sensor 12 may comprise a communication unit for wireless communication, such that the generated sequence of pressure measurements may be communicated wirelessly. For instance, the communication unit may be arranged to transmit radio frequency signals, e.g. using Bluetooth®.

According to an embodiment, the pressure sensor 12 may comprise a wired connection for communicating the generated sequence of pressure measurements. The plurality of pressure sensors 12 may be jointly connected such that the respective generated sequence of pressure measurements are communicated through a common wired connection.

Figure 2:
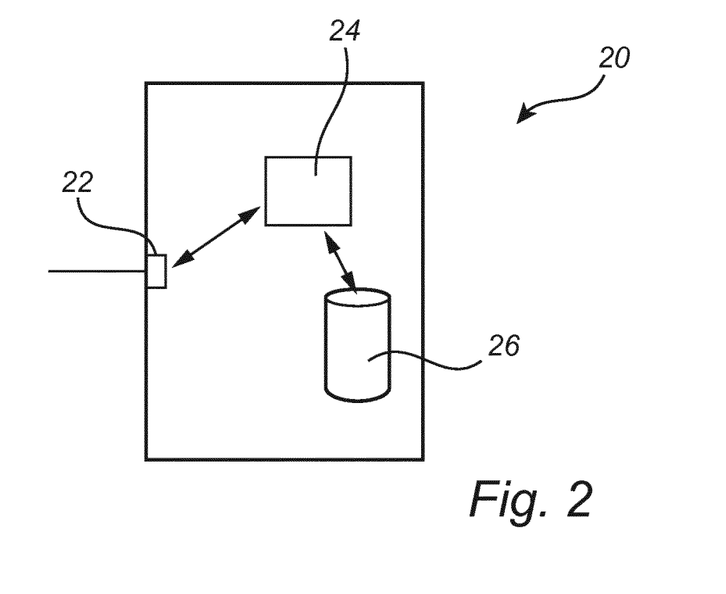
FIG. 2 is a schematic view of a control device in the system of FIG. 1.

As shown in more detail in FIG. 2, the system 10 may further comprise a control device 20. The control device 20 may be connected to the plurality of pressure sensors 12. Alternatively, the control device 20 may comprise an antenna for receiving wireless communication from the pressure sensors 12.

The generated sequences of pressure measurements may thus be received by at least one input contact 22 of the control device 20. The input contact 22 may thus receive a plurality of signals from the pressure sensors 12. Each signal may provide a time sequence of values representing asserted pressure on the respective pressure sensor 12.

The input contact 22 may further be connected to a processing unit 24 within the control device 20. The processing unit 24 may thus receive the plurality of signals and may process the signals. The signals may be processed for detecting a foot being lifted, as will be further explained below.

The processing unit 24 may be implemented as a microprocessor, which may be programmable for controlling operation of the microprocessor. For instance, the processing unit 24 may be a central processing unit (CPU). The processing unit 24 may alternatively be a special-purpose circuitry for providing only specific logical operations. Thus, the processing unit 24 may be provided in the form of an ASIC or FPGA.

The control device 20 may further comprise a non-volatile memory 26. The memory 26 may store application(s), which may be loaded into a working memory of the processing unit 24 for controlling the processing performed by the processing unit 24. The application(s) may for instance provide an algorithm for processing the received plurality of signals for determining when a foot is being lifted for walking.

The control device 20 may further be connected to an electrode (not shown) for providing electrical stimulation to the patient. The electrode may be attached to the patient, such that when an electrical pulse is provided through the electrode, the electrical pulse may induce a withdrawal reflex of the patient. For instance, the electrode may be arranged under the foot sole of the patient.

The processing unit 24 may be arranged to provide a trigger signal. The trigger signal may be sent to a pulse generating unit within the control device 20 for providing an electrical stimulation by the electrode. Alternatively, the pulse generating unit may be separate from the control device 20, and the trigger signal may be sent to the pulse generating unit through wired or wireless connection between the control device 20 and the pulse generating unit.

The control device 20 may be arranged in a housing containing electrical components of the control device 20. However, it should be realized that the control device 20 may be divided in a plurality of physical units.

The control device 20 may comprise a hook or any other attachment means arranged on an outer side of the housing such that the control device 20 may be attached to the patient or clothes of the patient during gait rehabilitation, or to a caregiver. For instance, the control device 20 may be suspended from a belt of the patient or the caregiver, or may be suspended around a neck of the patient or the caregiver.

The control device 20 may further provide a user interface, which allows input to the control device 20 for controlling functionality of the control device 20. For instance, the user interface may comprise buttons, switches and the like arranged on an outer side of the housing for allowing input to be made directly on the control device 20. Alternatively, the user interface may be provided as an application of an external unit, such as a mobile phone or computer, which may communicate with the control device 20.

A caregiver may input information to the control device 20 for controlling a rehabilitation program to be performed on a patient. The input may be parameters to the control device 20, such as an intensity of electrical stimulation to be provided or parameters for controlling a process of detecting a foot being lifted.

Figure 3:
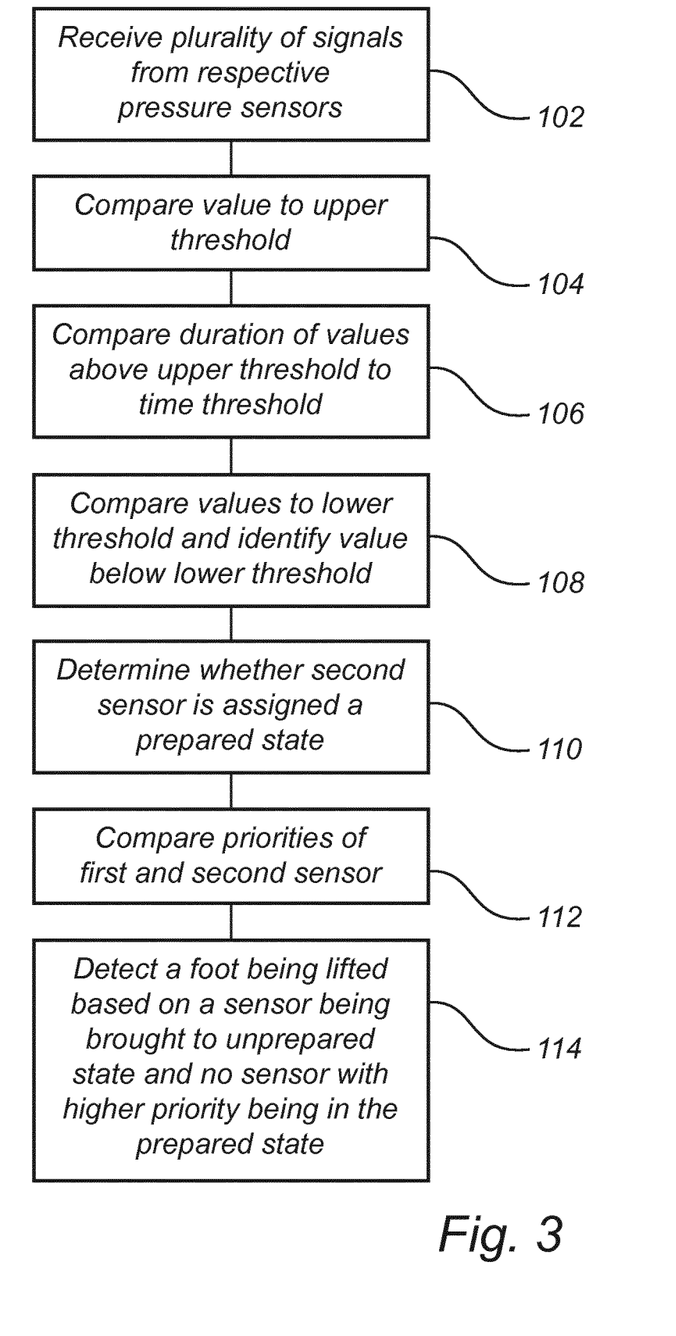
FIG. 3 is a flow chart of a method for detecting a foot being lifted.
Figure 4:
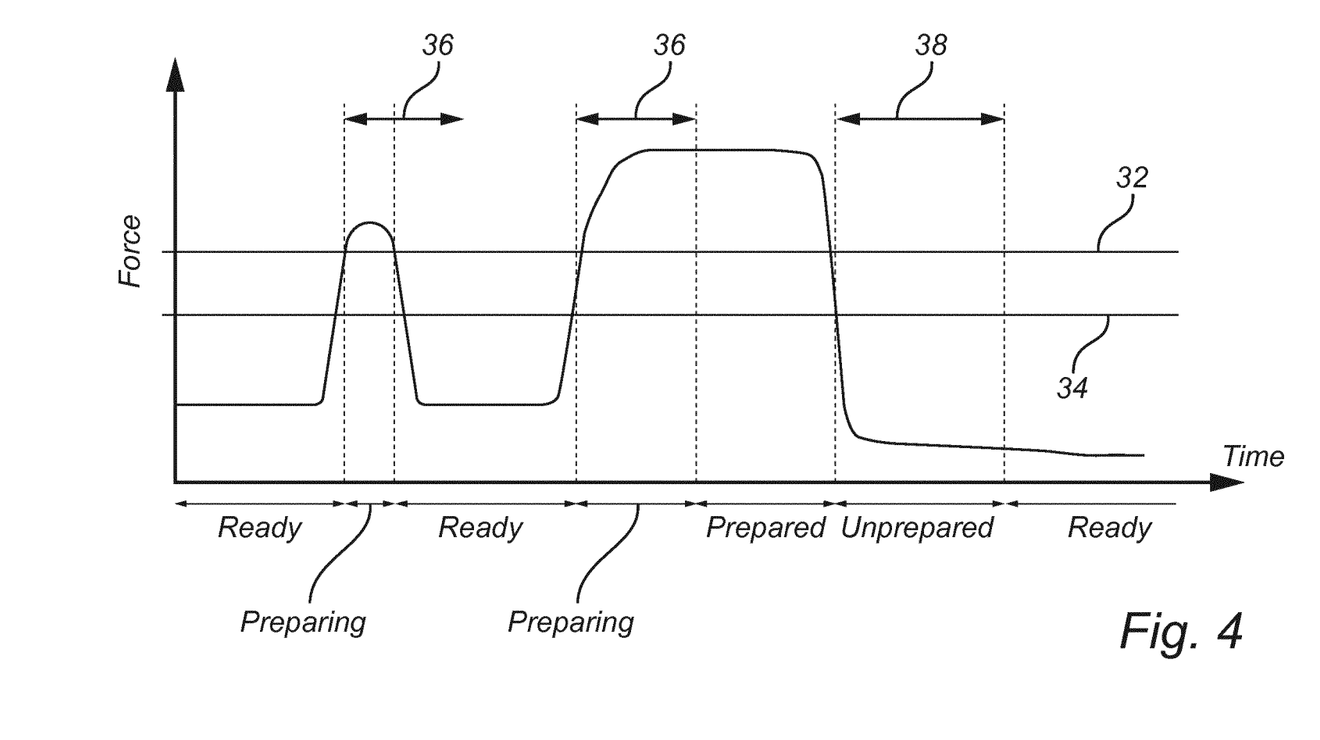
FIG. 4 is a chart illustrating a signal provided by a pressure sensor for detecting a foot being lifted.

Referring now to FIG. 3, a method for detecting a foot being lifted will be explained. The method comprises continuously receiving, step 102, a plurality of signals from respective pressure sensors 12. Each signal provides a time sequence of values representing asserted pressure on the respective pressure sensor 12. In FIG. 4, such a signal from one pressure sensor 12 is shown and the method will be explained in relation to the signal shown in FIG. 4.

Firstly, an upper threshold 32 and a lower threshold 34 are defined. These thresholds 32, 34 may be pre-defined in the algorithm or may be set by a caregiver. The thresholds are used for detecting that a change in state may be occurring as further explained below.

A state is assigned to the sensor 12, in dependence of values representing the asserted pressure. The assigned state of the sensor 12 may be used for determining when a foot is lifted.

Initially, the sensor 12 is assigned a "Ready" state. In the "Ready" state, the values representing asserted pressure are compared, step 104, to the upper threshold 32.

When it is identified that the value is above the upper threshold, the sensor 12 is assigned a "Preparing" state. This implies that the patient is preparing to take a step, as the foot is pressed down. In the "Preparing" state, the sequence of values are compared to the upper threshold 32 to ensure that the asserted pressure is above the upper threshold 32 for a substantial time period.

A duration during which the sequence of values are continuously above the upper threshold 32 is thus compared to a time threshold 36, step 106. If the values fall below the upper threshold 32 too early, the sensor 12 is again assigned the "Ready" state. However, if the values are maintained above the upper threshold 32 for a duration exceeding the time threshold 36, the sensor 12 is assigned a "Prepared" state.

This implies that the patient has now asserted a substantial pressure for a substantial time and is prepared to lift the foot for walking.

In the "Prepared" state, the sequence of values are compared to the lower threshold 34. When it is identified, step 108, that a value falls below the lower threshold 34, the identification may be used as an indication that the foot is potentially lifted. The sensor 12 is assigned an "Unprepared" state and is maintained in this state for a predetermined time period 38. Thereafter, the sensor 12 is again assigned the "Ready" state. The predetermined time period 38 is used to ensure that a certain time passes, before a new detection of the foot being lifted can be made. The sensor 12 can only be assigned the "Preparing" state from the "Ready" state.

In the above, the processing of a signal from a single pressure sensor 12 is described. However, the control device 20 receives signals from a plurality of sensors 12.

The plurality of sensors 12 may be provided with different priorities. This implies that the identification of an indication that the foot is potentially lifted based on a signal from a single pressure sensor 12 may be further analyzed in relation to states of other pressure sensors 12.

Thus, when a first sensor is assigned the "Unprepared" state, a determination is made, step 110, whether a second sensor is assigned a "Prepared" state. If so, the priorities of the first and the second sensors are compared, step 112.

If the second sensor has a higher priority, it is determined that the foot is not actually lifted. Rather, a large pressure is still asserted on a pressure sensor 12 having larger significance for the determination of the foot being lifted.

In an embodiment, three pressure sensors 12 may be used, including a heel sensor which is mounted on the heel, a lateral forefoot sensor which is mounted on the lateral forefoot and a medial forefoot sensor which is mounted on the medial forefoot.

The heel sensor may be assigned priority 2, whereas the lateral forefoot sensor and the medial forefoot sensor may be assigned priority 1.

This implies that if the heel sensor is in a "Prepared" state, the identification of an indication that the foot is potentially lifted based on the lateral forefoot sensor or the medial forefoot sensor is not given any weight. In such case, it is only when the heel of the patient is lifted that the detection of the foot being lifted for walking is made.

However, patients having impaired gait may not be able to bring the heel in contact with ground. Such patients may be walking merely with the forefoot in contact with ground. Thanks to the lateral forefoot sensor and medial forefoot sensor being used with a different priority than the heel sensor, these lateral forefoot and medial forefoot sensors may be used for detecting a patient with impaired gait lifting the foot for walking. Still the lateral forefoot and medial forefoot sensors may not trigger a detection of the foot being lifted for a patient using the heel in contact with ground during walking.

If a sensor 12 is brought to the "Unprepared" state and it is determined that no other sensor 12 is in the "Prepared" state or no sensor 12 with a higher priority is in the "Prepared" state, a detection that the foot is being lifted is made, step 114.

The detection that a foot is lifted may cause the processing unit 24 to provide a trigger signal for providing an electrical stimulation by the electrode. Thus, the patient may be provided with an electrical stimulation helping the patient to lift the foot for walking.

When it is detected that a foot is lifted, all sensors 12 are assigned the "Unprepared" state, regardless of their previous state, and maintained in this state for the predetermined time period 38. However, if the value representing asserted pressure is above the lower threshold 34, which may occur for a sensor 12 having lower priority than the sensor 12 causing detection of the foot being lifted, the sensor 12 is maintained in the "Unprepared" state as long as the values representing asserted pressure are above the lower threshold 34. When the value representing asserted pressure falls below the lower threshold 34, the predetermined time period 38 starts and the sensor 12 is maintained in the "Unprepared" state until the predetermined time period 38 has expired.

The time threshold 36 and the predetermined time period 38 may be pre-defined in the algorithm or may be set by a caregiver as parameters to be used for a session of gait rehabilitation.

The time threshold 36 should not be too short, such that a detection of lifting of a foot may be made due to the patient very briefly asserting a high pressure on a pressure sensor 12. However, the time threshold 36 should not be too long, such that the algorithm may miss to detect a foot being lifted, due to the sensor never being assigned the "Prepared" state. In one embodiment, the time threshold 36 may be set to 70 ms. In another embodiment, the time threshold 36 may be set to 100 ms.

The predetermined time period 38 should not be too short, such that a detection of lifting of a foot may be falsely made, e.g. shortly after a heel being lifted, another detection may be made based on the forefoot being lifted. However, the predetermined time period 38 should not be too long, such that the algorithm may miss to detect a foot being lifted, due to the algorithm not being ready to make a detection when a subsequent lifting of the foot is made. In one embodiment, the predetermined time period 38 may be set to 150 ms. This may be suitable for a patient having a relatively normal gait. In another embodiment, the predetermined time period 38 may be set to 400 ms, or even 500 ms, which may be suitable for a patient having severely impaired gait.

The priorities of the pressure sensors 12 may be pre-defined in the algorithm or may be set by a caregiver as parameters to be used for a session of gait rehabilitation.

For instance, the pressure sensors 12 may be adapted for specific placement in relation to the foot, e.g. by all the pressure sensors 12 being arranged on a common carrier, which may have a shape corresponding to a foot. It may thus be known for each signal, at which position on the foot the respective pressure sensor 12 is arranged, and the algorithm may thus be provided with pre-defined priorities for handling the signals accordingly.

However, if the pressure sensors 12 are individually positioned by a caregiver before a session of gait rehabilitation, the caregiver may also define the priorities in order for the algorithm to correctly interpret received signals.

Further, it should be realized that the caregiver may define other priorities to pressure sensors 12 depending on the gait of the patient to adapt the detection of lifting of a foot to the specific patient.

In the above the invention has mainly been described with reference to a limited number of embodiments. However, as is readily appreciated by a person skilled in the art, other embodiments than the ones disclosed above are equally possible within the scope of the invention, as defined by the appended claims.

The invention claimed is:

1. A gait rehabilitation system, comprising:
at least first and second pressure sensors mounted beneath a foot of a person, each sensor configured to repeatedly determine a pressure exerted by the person against a surface and send a signal comprising data regarding a pressure intensity and a pressure duration; and
a processor configured to:
receive a signal from the first sensor and assign one of a weight-detected state, a reset state, or a lift state to the first sensor, provided that:
a weight-detected state is assigned only when the pressure intensity and the pressure duration both exceed predetermined thresholds;
a lift state is assigned when the pressure intensity falls below a predetermined threshold after the sensor has been assigned the weight-detected state; and
a reset state is assigned after a predetermined time period elapses after the sensor has been assigned the lift state;
receive a signal from the second sensor and assign one of a weight-detected state, a reset state, or a lift state to the second sensor, provided that a lift state is not assigned to the second sensor if the weight-detected state is assigned to the first sensor and a predetermined priority of the first sensor is higher; and
determine, based on at least one of the first or second sensors being assigned the lift state, that the foot is being lifted.

2. The gait rehabilitation system of claim 1, wherein the processor is further configured to automatically assign the reset state after the predetermined time period is greater than 150 ms.

3. The gait rehabilitation system of claim 1, wherein the processor is further configured to assign a weight-detected state only if the previously assigned state is a reset state.

4. The gait rehabilitation system of claim 1, wherein the processor is further configured to receive an indication of the priority of each of the pressure sensors.

5. The gait rehabilitation system of claim 1, wherein the predetermined priority is based on a sensor's position with respect to an anatomical region of the foot.

6. The gait rehabilitation system of claim 5, wherein a higher priority is assigned to a sensor at a heel of the foot.

7. The gait rehabilitation system of claim 1, further comprising an electrode mounted beneath the foot of the person for providing an electrical pulse to the person upon receiving a trigger signal from the processor.

8. The gait rehabilitation system of claim 7, wherein the processor is further configured to send the trigger signal when the processor determines that the foot is being lifted.

9. The gait rehabilitation system of claim 8, wherein the processor is further configured to assign a lift state to all of the pressure sensors when the trigger signal is sent.

10. The gait rehabilitation system of claim 1, wherein the pressure duration is greater than at least 70 ms.

11. The gait rehabilitation system of claim 1, wherein a reset state is maintained until a weight-detected state is assigned.

12. The gait rehabilitation system of claim 1, wherein the at least first and second pressure sensors comprise a heel sensor, a lateral forefoot sensor, and a medial forefoot sensor.

13. A method, comprising:
receiving, from at least first and second pressure sensors mounted beneath a foot of a person, signals comprising data regarding a pressure intensity and a pressure duration exerted by the person against a surface;
assigning, to the first sensor, one of a weight-detected state, a reset state, or a lift state, provided that:
a weight-detected state is assigned only when the pressure intensity and the pressure duration both exceed predetermined thresholds;
a lift state is assigned when the pressure intensity falls below a predetermined threshold after the sensor has been assigned the weight-detected state; and
a reset state is assigned after a predetermined time period elapses after the sensor has been assigned the lift state;
assigning, to the second sensor, one of a weight-detected state, a reset state, or a lift state, provided that a lift state is not assigned to the second sensor if the weight-detected state is assigned to the first sensor and a predetermined priority of the first sensor is higher; and
determining, based on at least one of the first or second sensors being assigned the lift state, that the foot is being lifted.

14. The method of claim 13, further comprising automatically assigning the reset state after the predetermined time period is greater than 150 ms.

15. The method of claim 13, further comprising receiving an indication of the priority of each of the pressure sensors.

16. The method of claim 13, wherein the predetermined priority is based on a sensor's position with respect to an anatomical region of the foot.

17. The method of claim 13, further comprising sending a trigger signal when determining that the foot is being lifted.

18. The method of claim 17, further comprising assigning a lift state to all of the pressure sensors when the trigger signal is sent.

19. The method of claim 13, further comprising maintaining a reset state for each sensor until a weight-detected state is assigned.

20. A gait rehabilitation system, comprising:
a processor configured to:
receive a signal comprising data regarding a pressure intensity and a pressure duration from a first sensor mounted beneath a foot of a person;
assign one of a weight-detected state, a reset state, or a lift state to the first sensor, provided that:
a weight-detected state is assigned only when the pressure intensity and the pressure duration both exceed predetermined thresholds;
a lift state is assigned when the pressure intensity falls below a predetermined threshold after the sensor has been assigned the weight-detected state; and
a reset state is assigned after a predetermined time period elapses after the sensor has been assigned the lift state;

receive a signal comprising data regarding a pressure intensity and a pressure duration from a second sensor mounted beneath the foot of the person;

assign one of a weight-detected state, a reset state, or a lift state to the second sensor, provided that a lift state is not assigned to the second sensor if the weight-detected state is assigned to the first sensor and a predetermined priority of the first sensor is higher; and determine, based on at least one of the first or second sensors being assigned the lift state, that the foot is being lifted, and determine, based on the determination that the foot is being lifted, to send a trigger signal to stimulate a withdrawal reflex of the foot.

\* \* \* \* \*